(12) United States Patent
Ivansson et al.

(10) Patent No.: US 11,802,297 B2
(45) Date of Patent: Oct. 31, 2023

(54) METHOD FOR CELL LINE DEVELOPMENT

(71) Applicant: GE Healthcare Bio-Sciences AB, Uppsala (SE)

(72) Inventors: Daniel Ivansson, Uppsala (SE); Andreas Castan, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 556 days.

(21) Appl. No.: 16/490,623

(22) PCT Filed: Feb. 23, 2018

(86) PCT No.: PCT/EP2018/054466
§ 371 (c)(1),
(2) Date: Sep. 3, 2019

(87) PCT Pub. No.: WO2018/158142
PCT Pub. Date: Sep. 7, 2018

(65) Prior Publication Data
US 2020/0002728 A1    Jan. 2, 2020

(30) Foreign Application Priority Data

Mar. 3, 2017  (GB) .................................. 1703418

(51) Int. Cl.
*C12N 15/90* (2006.01)
*C12N 9/12* (2006.01)
*C12P 21/00* (2006.01)
*C07K 16/00* (2006.01)

(52) U.S. Cl.
CPC ............ *C12N 15/907* (2013.01); *C07K 16/00* (2013.01); *C12P 21/00* (2013.01); *C12N 2510/02* (2013.01)

(58) Field of Classification Search
None
See application file for complete search history.

(56) References Cited

U.S. PATENT DOCUMENTS 11,136,598 B2 * 10/2021 Ivansson ............. C12N 15/907
2015/0167020 A1 * 6/2015 Rance .................... C07K 16/00
435/15

FOREIGN PATENT DOCUMENTS

| WO | 02/057423 A2 | 7/2002 |
| WO | 2004/009823 A1 | 1/2004 |
| WO | 2004/029284 A2 | 4/2004 |
| WO | 2009/118192 A1 | 10/2009 |
| WO | 2009/130598 A1 | 10/2009 |
| WO | 2012/138887 A1 | 10/2012 |
| WO | 2014/205192 A2 | 12/2014 |

OTHER PUBLICATIONS

Nehlsen et al., BMC Biotechnol. 9:100, 2009, 12 pages (Year: 2009).*
PCT International Search Report and Written Opinion for PCT Application No. PCT/EP2018/054466 dated May 16, 2018 (13 pages).
Great Britain Search Report for GB Application No. 1703418.2 dated Dec. 21, 2017 (8 pages).
Baer et al., "Coping with Kinetic and Thermodynamic Barriers: RMCE, an Efficient Strategy for the Targeted Integration of Transgenes," Current Opinion in Biotechnology, 2001, 12:473-480.
Bandaranayake et al., "Recent Advances in Mammalian Protein Production," FEBS Letters, 2014, 588:253-260.
Schucht et al., "Rapid Establishment of G-Protein-Coupled Receptor-Expressing Cell Lines by Site-Specific Integration," Society for Laboratory Automation and Screening, 2011, pp. 323-331.
Wirth et al., "Road to Precision: Recombinase-Based Targeting Technologies for Genome Engineering," Current Opinion in Biotechnology, 2007, 18:411-419.
Zhang et al., "Recombinase-Mediated Cassette Exchange (RMCE) for Monoclonal Antibody Expression in the Commercially Relevant CHOK1SV Cell Line," Biotechnol. Prog., 2015, 11 pages.

* cited by examiner

*Primary Examiner* — David Steadman
(74) *Attorney, Agent, or Firm* — Eversheds Sutherland (US) LLP

(57) ABSTRACT

The present invention relates to an improved method for cell line development (CLD) which is generally applicable to production of any therapeutic protein that can be produced using mammalian Cell lines and in particular Chinese Hamster Ovary (CHO) cells. The method combines site-directed integration (SDI), expression construct components improving the post-transcriptional processing of the gene of interest (GOI) and the introduction of a onetime pre-CLD host cell line selection workflow to generate a production competent cell line that can then be used in multiple CLD efforts using SDI from that point on.

11 Claims, 9 Drawing Sheets

METHOD FOR CELL LINE DEVELOPMENT

CROSS REFERENCE TO RELATED APPLICATIONS

This application claims the priority benefit of PCT/EP2018/054466 filed on Feb. 23, 2018, which claims priority benefit of European Application No. 1703418.2 filed on Mar. 3, 2017. The entire contents of which are hereby incorporated by reference herein.

FIELD OF THE INVENTION

The present invention relates to an improved method for cell line development which is generally applicable to production of any therapeutic protein that can be produced using mammalian Cell lines and in particular Chinese Hamster Ovary (CHO) cells.

BACKGROUND OF THE INVENTION

During the latest 30 years recombinant protein therapeutics has evolved from a novelty to a dominating position among marketed drugs. Recombinant production of therapeutic proteins has surpassed the 100 billion $ per year market volume and plays an important role in the global economy as well as in advanced medical care. The therapeutic protein class includes replacement proteins (insulin, growth factors, cytokines and blood factors), vaccines (antigens, VLPs) and monoclonal antibodies. The by far dominating format is the monoclonal antibodies. Some of the recombinant proteins can be produced in simple microbial cells such as *E. coli*, but for more complex proteins including the monoclonal antibody class Chinese Hamster Ovary (CHO) cells is the dominating host for production [1]. The monoclonal antibody class is projected to continue being the dominating format but with a larger heterogeneity in molecular structure within this class including different multi-specific formats, fusion proteins, alternative scaffolds and antibody drug conjugates (ADCs). However, since most of these formats will still require advanced protein processing capacity (including glycosylation, disulfide formation and advanced folding machinery) not offered by microbial cells, CHO will likely continue to be the dominating production host for many years to come.

Increased knowledge about the molecular details underlying human diseases has revealed a huge heterogeneity of main diagnoses. As an example, breast cancer is no longer considered to be one disease but consists of at least several 10s of sub-diagnoses. Hence, protein therapeutics is becoming more targeted towards specific molecular mechanisms and will most likely be even more so in the future. Thus an increased number of drugs are needed to enable treatment of whole populations displaying different variants of disease at the molecular level. At the same time there is an increasing pressure to decrease the cost of healthcare, including drugs. Major contributors to the cost of therapeutic protein drugs are the long development time and frequent late failure of drug candidates. One approach to mitigate the risk of late failure and increase the development speed is to evaluate multiple drug candidates early for their developability potential (titer in intended production host, aggregation tendency, formulation stability, immunogenicity). For this to work the production of early protein material must be highly similar to the intended final process and require a minimum of time and effort. For complex protein therapeutics the final production is generally performed in a clonal CHO cell line carrying the recombinant genes stably inserted into the genome by a process referred to as Cell Line Development (CLD).

Currently the mainstream approach to cell line development using e.g. CHO (Chinese hamster ovary) cells is to use random integration of genes of interest followed by (a) selection of cells having the GOI (gene of interest) integrated and (b) a massive screening of clones to find specific clones with favorable production characteristics. The reasons why screening is needed is twofold (i) As a GOI is integrated randomly into the genome the resulting transcription level will be impacted by epigenetic regulation in the region of insertion. A clone having the GOI integrated into one or several highly active and stable genomic locations is needed. Typical cell lines generated generally contain between 5-20 copies of the GOI. (ii) A clone adapted to the burden of expressing a foreign protein at very high levels and with maintained good growth characteristics is needed. However, a CHO host cell is, for example, not a very competent secretor. Further, the CHO genome is highly plastic. By introducing expression of foreign secreted proteins at very high levels an evolutionary pressure towards increased folding and secretory capacity is introduced. By screening many clones, cells better adapted for high secretion can be found. The best random integration platforms today can yield high protein titers in a relatively short time period (~3 months) albeit using a very resource intensive workflow. Further, generated cell clones will be different at the genetic and phenotypic level between different cell line development efforts. This makes early developability assessment to improve efficiency of development difficult and increases process development efforts.

One potentially major improvement is to utilize targeted integration (site-directed integration; SDI) of genes of interest. In such a scenario a pre-identified genomic location known to support high and stable transcription is used as a target destination for GOIs in all CLD efforts. Using intelligent combinations of pre-introduced sequences and vector designs, including the use of co-transfected nucleic acid enzymes such as nucleases or recombinases, will facilitate targeted insertion and ensure that all cells in culture will contain correctly inserted GOIs and hence have a high transcription rate [2-4]. This will significantly reduce the number of clones in the screening campaign. All clones will have the same relatively high transcription rate and hence all clones will also have an evolutionary pressure towards improved handling of the recombinant protein production burden. However, at least two challenges remain (1) SDI generally only integrates a single copy of the GOI and hence the level of expression and evolutionary pressure is generally lower than what can be achieved using random integration and (2) one still need to find a clone that has undergone genetic changes adapting it to e.g. high secretion etc.

SDI ensures a similar level of transcription for both different clones following a specific transfection of a GOI and between different transfections, even using different GOIs. However, numerous changes exist at the genetic and phenotypic level between a typical host cell line lacking recombinant genes in its genome and the final production clone selected during CLD [5]. These differences represent the transformation towards an increased capacity to handle the metabolic burden of producing a foreign recombinant protein at very high levels. Changes will likely include an increased capacity for (i) amino acid synthesis and tRNA charging (ii) protein folding and (iii) protein secretion together with an efficient basic metabolic phenotype. Finding the clone having undergone the desired transformation generally requires substantial screening. The CHO genome is highly plastic and this plasticity forms the engine for introducing variation for screening. However, it is highly likely that the evolutionary pressure of high recombinant protein expression is needed as an inherent selection agent to guide and maintain accumulation of a large number of changes beneficial for recombinant protein production (and avoid accumulation of negative changes) in a single clone.

Thus, to increase speed and enable highly parallel developability assessments, there exists a need of an improved method for cell line development that reduces the need for screening and generates more similar cells between campaigns.

SUMMARY OF THE INVENTION

The present invention provides an improved and novel method for cell line development. The method combines SDI, expression construct components improving the post-transcriptional processing of the GOI and the introduction of a onetime pre-CLD host cell line selection workflow to generate a production competent cell line that can then be used in multiple CLD efforts using SDI from that point on.

In a first aspect the invention provides a method for creating a mammalian cell bank for cell line development comprising the following steps:
  (a) providing a recombinant mammalian cell comprising
    (i) a genomic region that is transcriptionally active during suspension culture of said recombinant cell in a serum free culture medium (ii) a recombinant template DNA construct integrated at said genomic region, said recombinant template DNA construct having a region containing elements needed for expression of a template protein of interest and one or several sequence elements enabling excision of said template protein of interest region from said template DNA construct and optionally the simultaneous introduction of a region from a donor DNA construct into said template DNA construct;
  (b) based on said recombinant cell generating one or several candidate cells or cell populations;
  (c) measuring production traits of said generated candidate cells or cell populations and selecting a top candidate cell or cell population having improved characteristics for production of said template protein of interest;
  (d) optionally providing a donor DNA construct containing (1) one or several sequences enabling the integration of a region from said donor DNA construct into said template DNA construct (2) said donor DNA region further containing one or several sequence elements Q enabling the introduction of an expression vector DNA construct into said donor DNA region;
  (e) treating said top candidate cell or cell population with a DNA processing enzyme excising said template protein of interest coding region from said top candidate cell or cell population and optionally simultaneously introducing said donor DNA region by targeted integration into said top candidate cell or cell population resulting in the creation of a receiving DNA construct with one or several functional sequence elements Q enabling the targeted introduction of said expression vector DNA construct into said receiving DNA construct;
  (f) selecting a final cell or cell population were all cells have undergone correct modification only; and
  (g) from said final cell or cell population creating a cell bank for cell line development, wherein said expression vector DNA construct comprises a region encoding a desired protein of interest belonging to the same class as said template protein of interest, and wherein expression of said desired protein of interest is achieved by using an expression vector to introduce said expression vector DNA construct into said receiving DNA construct at said genomic region of a cell or cell population derived from said cell bank.

The same class in respect of protein of interest and template protein refers to a group of proteins sharing a common sequence or structural feature. Examples of protein classes include antibodies of the same class (such as IgG1 antibodies), fusion proteins sharing at least one conserved domain (such as FC-fusion proteins), or in general proteins sharing a conserved scaffold sequence were sequence variation is introduced only at defined region.

In the above method preferably;
(a) said template DNA construct comprises in 5' to 3' sequence order a first recombinase recognition sequence, such as an attP or attB sequence, a first copy of a second recombinase recognition sequence, such as a loxP sequence, a promoter less selection marker gene and a region coding for a template protein of interest in any order and orientation followed by an additional copy of said second recombinase recognition sequence, such as a second loxP sequence; and
b) the promoter driving said promoter less selection marker gene can be placed upstream of said first recombinase recognition sequence or between said first recombinase recognition sequence and said first copy of said second recombinase recognition sequence or downstream of said second copy of said second recombinase recognition sequence; and
(c) said first and second recombinase recognition sequences act as recognition sequences for different recombinases; and
(d) said receiving DNA construct is created by the introduction of a vector coding for a recombinase with specificity for said second recognition sequence, such as Cre, catalyzing excision of the region being flanked by said second recombinase recognition sequences and leaving only a single second recombinase recognition sequence, such as a loxP sequence, downstream of said first recombinase recognition sequence; and
(e) said final cell or cell population is selected based on lack of selection marker activity and/or genetic characterization.

The candidate cell or cell populations may for example be generated according to any of the following procedures:
(a) isolating clones from a culture of said recombinant cell or cell population or descendants thereof; or
(b) isolating pools or clones after (1) different culture time in a continuous culture format such as a perfusion culture or (2) different number of individual cultures starting with inoculation of a first culture using said recombinant cell or cell population or descendants thereof and using a volume from a finished culture to inoculate a next culture or (3) a combination of (1) and (2); or
(c) performing targeted engineering by applying gene editing methods to introduce, remove or modify genetic material in the genome of said recombinant cell or cell population or descendants thereof; or
(d) using an isolated clone from a culture of said recombinant cell or cell population or descendants thereof to inoculate a culture in procedure (b); or
(e) any combination of procedures (a) to (d).

Steps (a) to (c) above may be iterated in the following way prior to creating said cell bank:

(1) in a next iteration the top candidate cell population from previous step (c) is used as said recombinant mammalian cell in step (a) after having exchanged said template DNA construct for a modified template DNA construct having been modified to provide increased expression potential compared to modified template DNA constructs in earlier iterations; and (2) repeating (a)-(c) n times.

In the above method the template protein of interest is coded by a single gene of interest or two or more genes of interest.

In a preferred embodiment of the above method said receiving DNA construct is introduced into said genomic location in the following way:

(a) providing a receiving DNA construct introduction vector comprising said receiving DNA construct flanked by two sequences X' and Y' being homologous to two corresponding sequences X and Y in a template DNA construct containing cell and wherein said sequences X and Y are unique or rare in the genome of said template DNA construct containing cell and flanking said template DNA construct;

(b) defining a gene editing nuclease recognition sequence within said template DNA construct being unique or rare in the genome of said template DNA construct containing cell;

(c) a vector(s) coding for a gene editing nuclease, such as a zinc finger nuclease/meganuclease/TALEN or a CRISPR/Cas9 combination, with specificity for said gene editing nuclease sequence is introduced together with said receiving DNA construct introduction vector into a cell or a population of cells from said recombinant mammalian cell;

(d) said gene editing nuclease creating a double strand break at said gene editing nuclease sequence catalyzing integration of said receiving DNA construct by cellular DNA repair mechanisms such as homologous recombination;

(e) cells having undergone correct introduction are selected via the use of a selection marker and/or genetic characterization.

The mammalian host cell line is preferably a CHO cell line such as CHO DG44, CHO K1, CHO M, CHO-S or a CHO GS knockout cell line.

In a second aspect, the invention relates to a method for mammalian cell line development comprising the following steps:

(a) providing a cell or cell population from a mammalian cell bank developed according to the method described above and having (i) a version of said receiving DNA construct containing a sequence z2 being unique or rare in the total genome sequence of said cell or cell population (ii) two sequences X and Y flanking said receiving DNA construct and being unique or rare in the genome of said mammalian cell;

(b) providing a matching expression vector in the form of a plasmid containing sequences X' and Y being homologous to said sequences X and Y and wherein said sequences X' and Y' flanks a desired protein of interest coding region including promoter(s) and a second selection marker coding region including promoter(s;

(c) introducing vector(s) coding for a gene editing nuclease with specificity for said sequence z2 together with said expression vector into said cell or cell population and wherein said gene editing nuclease is designed using any available technology platform such as zinc finger nucleases, meganucleases, TALENs or CRISPR/Cas9 designs;

(d) said genome editing nuclease generates a double strand break at sequence z2 catalyzing exchange of the regions flanked by said sequences X and Y in said receiving DNA construct and X' and Y' in said expression vector via cellular DNA repair mechanisms;

(e) a cell or cells having undergone correct cassette exchange only are selected via the use of selection marker(s) and/or genetic characterization.

In an alternative the method for mammalian cell line development comprises the following steps:

(a) providing a cell or cell population from a mammalian cell bank developed according to the above described method and having aversion of said receiving DNA construct comprising two recombinase recognition sequences flanking a first selection marker coding region and wherein said recombinase recognition sequences are both of the same type such as a serine recombinase type such as attP/attB or a tyrosine recombinase type such as Lox, Rox or FRT;

(b) providing a matching expression vector in the form of a plasmid containing two recombinase recognition sequences flanking a desired protein of interest coding region and a second selection marker coding region in any order and orientation, and wherein said recombinase recognition sequences in the expression vector are of the same type as and matching said recombinase recognition sequences in said receiving DNA construct;

(c) introducing said expression vector together with vector(s) coding for a recombinase, and wherein said recombinase is of any type matching said recombinase recognition sequences in said receiving DNA construct and said expression vector such as one selected from the group of PhiC31, Cre, Dre, or Flp;

(d) said recombinase catalyzes the exchange of the regions flanked by said recognition sequences in said receiving DNA construct and said expression vector;

(e) a cell or cells having undergone correct cassette exchange only are selected via the use of selection marker(s) and/or genetic characterization.

In a further alternative the method for mammalian cell line development comprises the following steps:

(a) providing a cell or cell population from a mammalian cell bank developed according to the above described method and having a version of said receiving DNA construct comprising a single recombinase recognition sequence followed by an optional first selection marker coding region and wherein said recombinase recognition sequence is of type such as a serine recombinase type such as attP/attB or a tyrosine recombinase type such as Lox, Rox or FRT;

(b) providing a matching expression vector in the form of a plasmid containing a recombinase recognition sequence followed by a desired protein of interest coding region and a second selection marker coding region in any order, and wherein said recombinase recognition sequence in the expression vector is of the same type as and matching said recombinase recognition sequence in said receiving DNA construct;

(c) introducing said expression vector together with vector(s) coding for a recombinase, and wherein said recombinase is of any type matching said recombinase recognition sequences in said receiving DNA construct and said expression vector such as one selected from the group of PhiC31, Cre, Dre, or Flp;

(d) said recombinase catalyzes the integration of said expression vector at said recognition sequence in said receiving DNA construct resulting in the presence of a functional region for expression of said desired protein of interest; and (e) a cell or cells having undergone correct integration of the expression vector only are selected via the use of selection marker(s) and/or genetic characterization.

In yet a further alternative the method for mammalian cell line development comprises the following steps:
(a) providing a cell or cell population from a mammalian cell bank developed according to the above described method and having a version of said receiving DNA construct containing in 5' to 3' sequence order (i) a 5' to 3' directional promoter, a first recombinase recognition sequence such as attP or attB and a second recombinase recognition sequence such as loxP, or (ii) a first recombinase recognition sequence such as attP or attB, a 3' to 5' directional promoter and a second recombinase recognition sequence such as loxP, or (iii) a first recombinase recognition sequence such as attP or attB, a second recombinase recognition sequence such as loxP and 3' to 5' directional promoter, and wherein said first and second recombinase recognition sequences act as recognition sequences for different recombinases;
(b) providing a matching expression vector in the form of a plasmid containing in clockwise sequence order (i) a recombinase recognition sequence followed by a promoter less selection marker gene and a desired protein of interest coding region including promoters, or (ii) a promoter less anti clockwise encoded selection marker gene, a recombinase recognition sequence and a desired protein of interest coding region including promoters, and wherein said recombinase recognition sequences in the expression vector are of the same type as and matching said recombinase recognition sequences in said receiving DNA construct;
(c) introducing said expression vector together with vector(s) coding for a recombinase, and wherein said recombinase is of any type matching said recombinase recognition sequences in said receiving DNA construct and said expression vector such as one selected from the group of PhiC31, Cre, Dre, or Flp; and
(d) said recombinase catalyzes the targeted integration of said expression vector into said receiving DNA construct;
(e) a cell or cells having undergone correct integration only are selected via the use of selection marker(s) and/or genetic characterization.

DETAILED DESCRIPTION OF THE INVENTION

Figure 1:
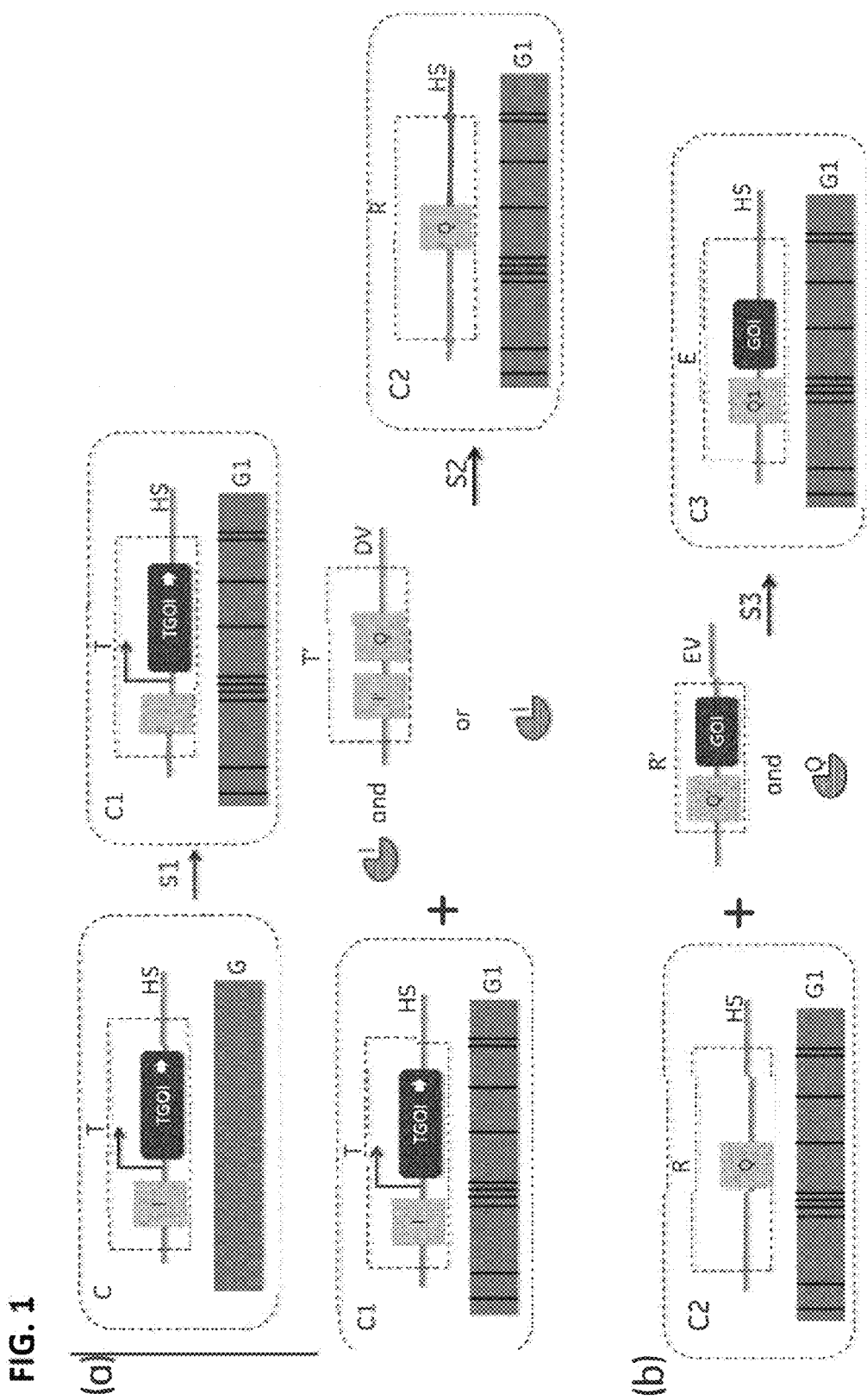
FIG. 1a describes a general workflow for generating a host cell line C2 with improved properties.
FIG. 1b describes a streamlined CLD workflow using the host cell line C2 for expression of a protein of interest.

The invention will now be described more closely in association with the accompanying drawings and some non-limiting Examples.

A unifying concept underlying the invention is the time limited utilization of an actively expressed template protein of interest for guiding the transformation of an initial mammalian host cell line having limited production capacity for a certain class of proteins into a high productivity host cell line that can be used for efficient production of any desired proteins of interest using Site-Directed Integration methods for CLD and were the desired protein of interest belongs to the same class as the template protein of interest. The invention includes methods enabling controlled removal of template protein of interest expression before expression of a desired protein of interest is initiated. Compared to potential methods using targeted engineering methods without the continuous expression of a template protein of interest to enable the desired transformation the current invention offers improvements in that the effects of single or multiple changes can be directly assessed using a protein indicative of the performance for a desired class of proteins and that the expression conditions used for the template protein of interest (mRNA levels and mRNA design) can be reproduced for any desired protein of interest.

In a preferred embodiment a key aspect of the invention is the opportunistic utilization of the inherent plasticity of the genome of typical mammalian host cell lines, such as the CHO genome, as an engine for generating epi-genetic and/or genetic changes enabling the desired transformation into a high productivity state and where the continuous high level expression of a template protein of interest during the transformation is used as an inherent selection agent and/or physiological state sensor directing and/or enabling detection of accumulation of positive changes leading towards the desired end goal. The potential for template protein of interest expression acting as an inherent selection agent is based on the fact that a high recombinant expression load imposed on all cells will have an impact on their viability and growth. Cells that do not handle the recombinant expression load well are hypothesized (and this is generally accepted in the field) to be subjected to stress responses (amino acid shortage, charged tRNA shortage, hold up of the ribosomal machinery of recombinant mRNAs, hold up of the folding machinery on recombinant proteins, build-up of soluble or aggregated forms of recombinant protein within cells) reducing viability and growth. Further, cells having genetic/epigenetic changes leading to an improved handling of the recombinant expression load are hypothesized to have a higher viability and growth. Hence, by culturing cells for many generations, far exceeding what is used in typical CLD workflows, a large diversity of genetic/epigenetic changes are sampled and enrichment of cells having accumulated multiple positive changes are hypothesized based on this directed evolution mechanism. An alternative way of screening through a massive diversity, far exceeding current scope in CLD workflows, is to utilize the template protein expression as a physiological state sensor and perform iterative stages of clone screening followed by periods of culturing. Each state of culturing introduces new diversity and diversity can also be increased above natural levels via the use of epi-genetic de-regulators or means to increase mutation rates.

In a further preferred implementation the genome of the improved host cell line is stabilized ("Frozen") using targeted gene editing methods [8] following the desired transformation. Compared to potential approaches using targeted engineering only to achieve the desired transformation the current invention offers potential large improvements. As shown in comparison of host cell lines and producer cell lines, generated using cell line development screening efforts, a large number of more or less subtle differences rather than a few dramatic differences exists between the low productivity and the high productivity state [5]. Examples known in the art has also shown limited success using single or a few targeted changes only and typically such changes yield competitive performance first after being combined with changes introduced using selection workflows (and hence the plasticity of genomes) following introduction of genes coding for a protein of interest [12]. Hence it is likely that a large number (10s to 100s) of more or less subtle changes spanning over many different cellular pathways are needed to transform for example a CHO cell to a high productivity state. Further it is likely that different protein classes will need at least partly different modifications for optimal performance. To achieve such large numbers of changes and changes with such precision in their effect will be highly challenging using targeting engineering approaches. First the desired changes must be understood and this will likely include a combination of major screening efforts and advanced systems biology modeling and even so combinatorial effects might easily be missed. Secondly, generating clones having the correct set of multiple changes will require a range of gene editing tools and major selection and screening. The approach based on utilizing the plasticity of host cell genomes during a pro-longed time period disclosed in the current invention offers a means to sculpture the complete genome to achieve the desired transformation without the need for massive screening to understand and define the changes needed or the need for a large range of costly genome editing reagents. Further, the postulated cost and resource effectiveness of the proposed approach could enable the generation of a range of host cell lines being adapted for the optimal production of different protein/biotherapeutic classes or even sub-groups with different characteristics (such as amino acid frequencies) within a given class. Finally, the non-targeted sculpturing of the genome can be combined with specific targeted changes introduced by genome editing. Such changes could include modulation/control of glycosylation, further boosting of specific parts of the secretion machinery, introduction of machinery for non-natural amino acids, introduction of machinery for specific post translational protein modifications and the already mentioned changes for stabilizing the genome of a host cell.

A typical limitation of SDI based CLD approaches utilizing a single copy of the GOI known in the art have been to reach high enough total protein translation rates. A typical cell line generated using random integration typically contains 5-20 copies of the GOI and hence gives a higher total protein translation rate based on higher mRNA levels. The single copy integration limits the maximum cell specific productivity obtainable using a specific recombinant gene construct design, but will also reduce the evolutionary pressure imposed on cells and is likely to negatively impact the selection of a high productivity phenotype as a lower expression load limits the detection of high performing phenotypes in a heterogenic population as the best phenotypes capable of expressing the protein well above the expression load cannot be distinguished from medium performance phenotypes just coping with the expression load. Hence, an important feature of the invention is to ensure a recombinant gene construct design enabling highly efficient mRNA translation to compensate for the lower mRNA levels or to use alternative promoters enabling increased mRNA levels from a single gene copy. In some embodiments this can be achieved by sequence designs promoting increased ribosome recruitment, increased translation initiation and optimized speed and minimized error rates in the translation elongation of the coding region. In a preferred embodiment of the method of the invention use is made of translational enhancement elements (TEEs) [6] in the 5'-UTR and RES-CUE modification [7] of the coding region.

With the combined solution described above (a pre-selected improved host cell line and improved translation and or promoters) competitive titers using single copy GOI integration should be possible and since screening of clones is expected to be at a minimum the time and resources needed for a CLD campaign will be significantly reduced allowing cost savings by shortened time to clinic and market. Since cells generated from different CLD efforts using different candidate constructs are expected to be highly similar both at the genetic and phenotypic level it will be possible to perform comparisons of developability traits (immunogenicity, protein titers, aggregation levels, protein self-association, binding specificity, formulation stability etc.) for an increased number of protein candidates in each drug development program and with stable cell lines identical to ones used in final production and without the data being corrupted by variation coming from differences in the physiological state of cell lines. This can in turn enable even larger cost savings and efficiency increases in drug development by increasing the likelihood of success and reducing the rates of late failures. In addition, by having control of the gene copy number, other expression elements of the GOIs and having increased control over the expression stability of GOIs more ambitious and pro-longed screening of host cell clonal diversity can be performed with potential to generate phenotypes with superior production traits for a certain protein class as compared to typical cell lines generated using random integration approaches or SDI approaches with modest screening known in the art. Finally an improved host cell line generated using any of the embodiments of the invention, potentially using significant efforts and resources, can be used for any desired number of CLD efforts using different desired proteins of interest of a similar protein class.

A conceptual general workflow for generating such a host cell line with improved properties can be found in FIG. 1a. First, an initial mammalian cell (C) carrying a single copy of a template DNA construct T, containing a fully functional template gene of interest (TGOI), at a defined location in the genome (HS) is provided. This cell is then put through a selection workflow (S1) to isolate/select a cell (C1) with highly increased capacity to produce the template protein of interest. The improved C1 cell will have a modified genome (G1) and/or transcriptome compared to the original cell genome (G) and/or transcriptome reflecting multiple accumulated changes in diverse cellular pathways and processes which together give rise to a phenotype with the improved expression capacity. In a following step the template DNA construct (T) of the improved cell C1 is modified to create a receiving DNA construct (R) lacking the TGOI but containing sequences Q enabling targeted integration of a desired gene of interest (GOI) from a matching expression vector (EV). This can either be achieved via the use of a DNA modifying enzyme (I) in solitude cutting out the TGOI containing region from T or via the combined use of a DNA modifying enzyme (I) and a donor DNA construct vector (DV). The resulting cell C2 will contain a receiving DNA construct (R) carrying sequences Q enabling site directed integration of a GOI. C2 can then be used in a streamlined CLD workflow (FIG. 1b) in which C2 is contacted with an expression vector (EV) containing a matching recombinant construct R' enabling a targeted integration of a desired protein of interest gene by introduction of R' from EV with the aid of a DNA modifying enzyme with specificity for Q (Q) to create a cell C3 maintaining the expression phenotype and genome (G1) of C2 but now expressing the desired protein of interest. The genomic location should preferably be a hot spot region, meaning that it supports high transcription of introduced genes and that this transcription is stable over time and reproducible for different genes and different culture conditions. Especially the transcription activity should be high and stable using a serum free culture medium and growth during suspension conditions. Hot spot regions can be identified either via screening approaches, bioinformatics or a combination of these. The current invention builds on that a defined genomic location has been selected and that the sequence of this genomic site is known. The template DNA construct T contains a TGOI and optionally gene(s) coding for selection marker(s) (SM(s)). Preferably the TGOI design contains genetic elements either outside or inside the coding sequence(s) providing a high level translation power for the corresponding protein to maximize the expression load/potential. Such elements can include strong promoters such as mCMV, hCMV or synthetic promoters [13], 5'-UTR designs providing increased mRNA stability and/or increased translation, 3'-UTR designs providing increased mRNA stability and/or increased translation, signal peptides providing improved secretion properties and optimized sequence stretches in coding regions based on synonymous codon changes. Preferentially, design of these sequence elements are based on TEEs in the 5'-UTR and RESCUE-modification of the coding region [6, 7].

Figure 2:
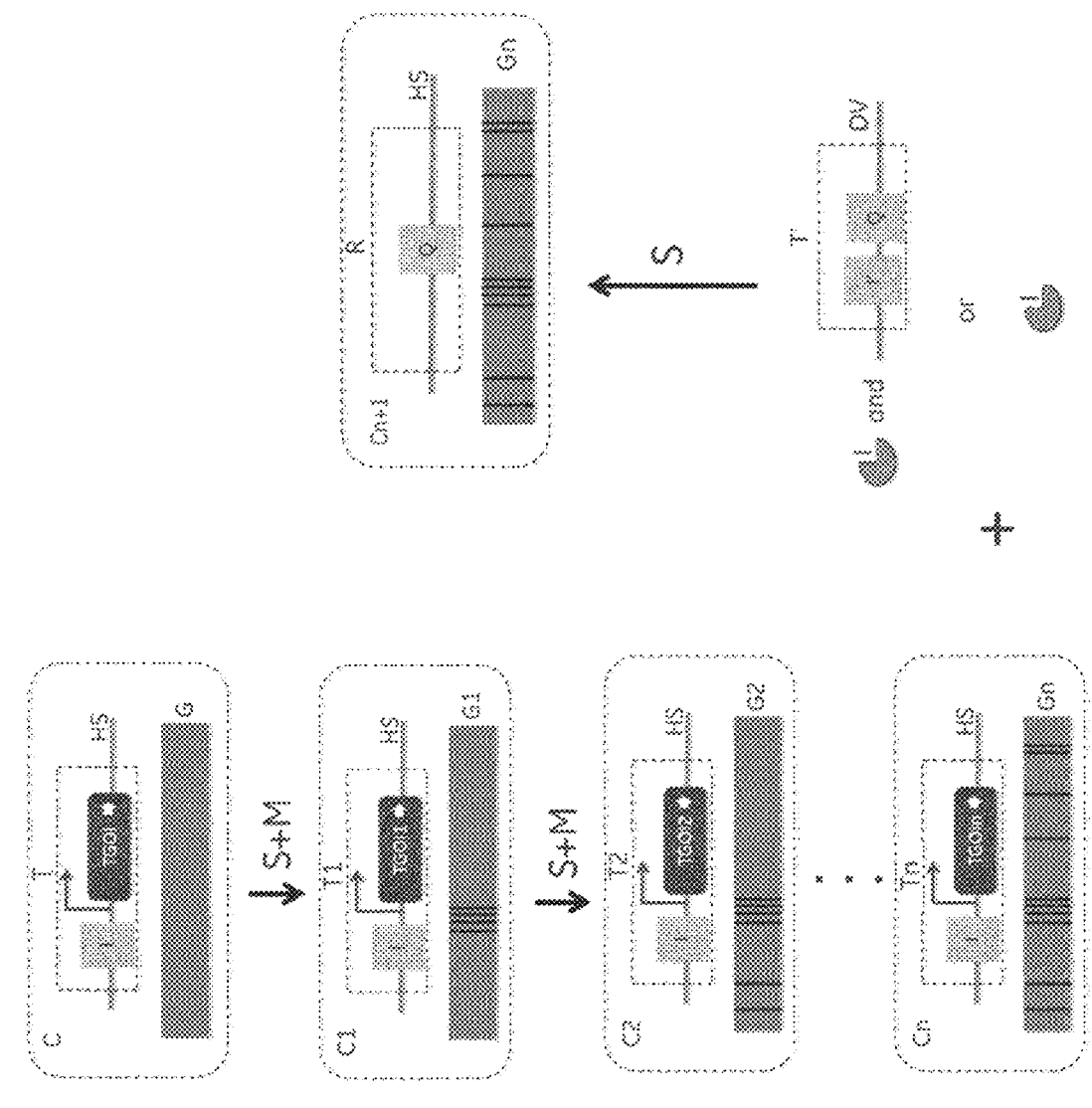
FIG. 2 is an alternative to FIG. 1 and describes generation of an improved cell line Cn+1 using an iterative workflow wherein the isolation/selection steps are repeated multiple times using a gradually increased expression load.
Figure 4:
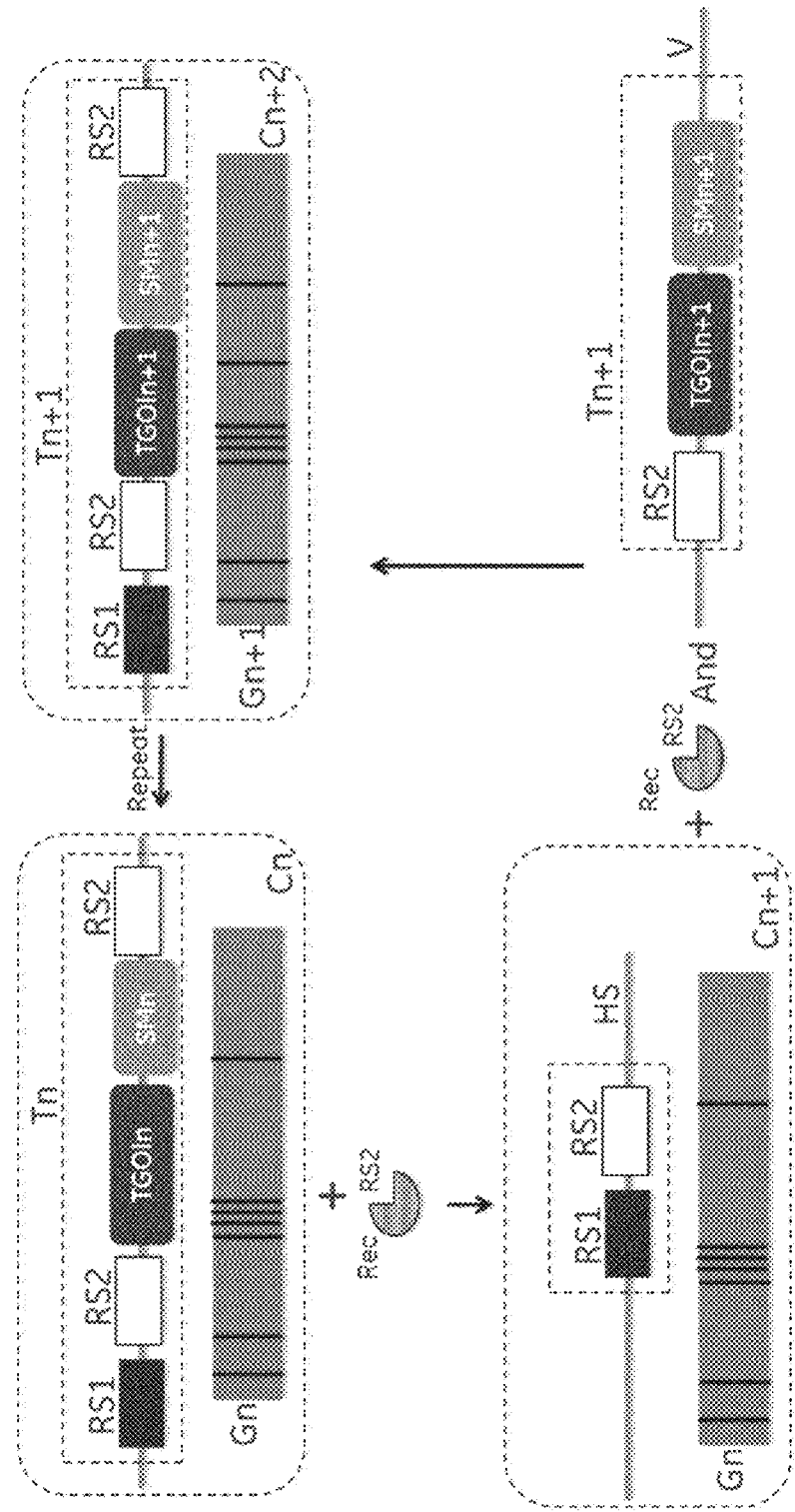
FIG. 4 describes a specific embodiment of the iterative approach described in FIG. 2 wherein a reversible recombinase (Rec-RS2) is used for both insertion and excision of TGOIs with increasing expression load for each iteration.
Figure 6:
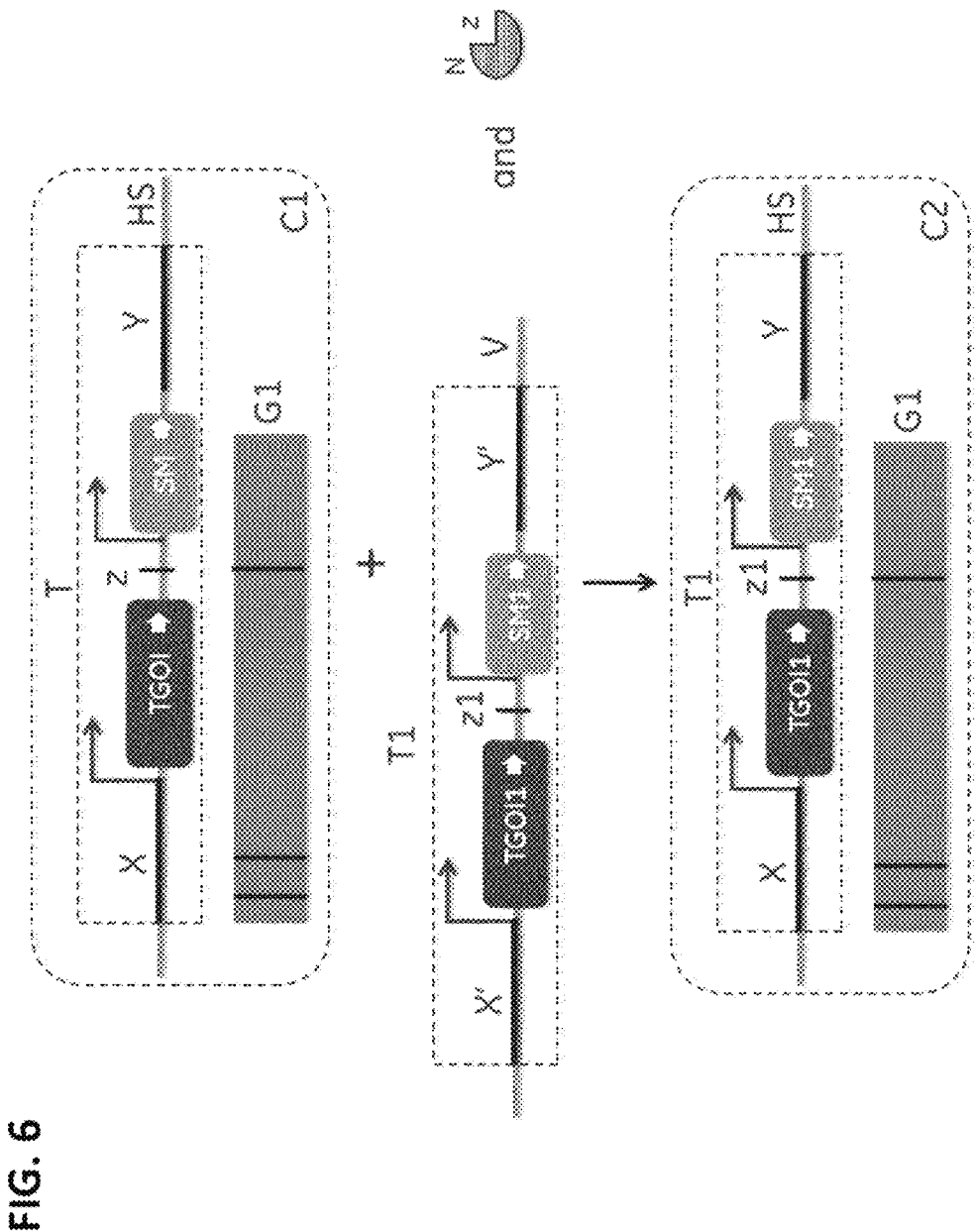
FIG. 6 describes one specific embodiment of the iterative approach described in FIG. 2 wherein cassette exchange is utilized mediated by a double strand break inducing site specific nuclease.

The generation of an improved cell can either be performed using a single TGOI expression load as outlined in FIG. 1 or by an iterative improvement workflow in which the expression load is gradually increased and intermittent improved cells are isolated after each increase in expression load until a final improved cell is generated as outlined in FIG. 2. In this workflow the first step improved cell carrying a recombinant DNA construct T enabling a first TGOI expression load is contacted with exchange vector(s) enabling modification of T including introduction of a new template DNA construct T1 enabling a second higher TGOI expression load. This in turn enables the selection of a second step improved cell. This gradual increase in expression load can be repeated any number of times until a final improved cell is generated. The expression load can be varied by using different promoter strengths in different TGOI construct generations, by utilizing 5'-UTR and 3'-UTR variants promoting different mRNA stability and/or translational efficiency, by utilizing coding sequences promoting different mRNA stability and/or translational efficiency or by changing the TGOI copy number between different generations. One specific embodiment of this iterative approach is to utilize cassette exchange mediated by a double stand break inducing site specific nuclease (Nz) as outlined in FIG. 6. Here the template DNA construct T contains a sequence X at the 5'-end, a sequence Y at the 3'-end and an internal sequence z. All sequences X, Y and z are unique or rare in the genome (G1) of cell C1. To exchange T for T1 the cell C1 is contacted with an exchange vector V carrying T1 and a site specific nuclease (Nz) with specificity for z. T1 contain sequences at the ends that are either identical to or highly similar to the sequences X and Y in T. The site specific nuclease creates a double strand break at z catalyzing cassette exchange between T and T1 via homologous recombination repair mechanisms using T1 as a repair template. If additional cassette exchange reactions are planned T1 should also contain a sequence z1 being unique or rare in the genome (G1) to enable cassette exchange using a second site specific nuclease with specificity for z1. The site specific nuclease can be any type of gene editing solution such as zinc finger nucleases, homing endonucleases, TALENs or CRISPR/Cas9 variants. An alternative to using gene editing assisted homologous recombination for exchanging TGOI variants is to utilize reversible recombinase systems, see FIG. 4, such as solutions based on Cre/loxP (RS2/Rec-RS2 in general terms) in which a TGOI variant (TGOIn) can be introduced at a loxP (RS2) sequence via the aid of the Cre recombinase (Rec-RS2) resulting in an introduced TGOI flanked by two loxP (RS2) sequences. Following isolation of an improved cell the previous generation TGOI can be removed via the action of Cre (Rec-RS2) which re-creates the single loxP (RS2) sequence enabling introduction of a new generation TGOI.

Two main approaches can be used to isolate an improved cell from an initial TGOI carrying cell. The first approach utilizes the inherent plasticity of the genome of typical mammalian host cell lines used for recombinant protein production. One embodiment of this approach to generate an improved cell line with improved properties is to screen clones from a culture for a desired set of protein production traits and select the top performing clone. Protein production traits could be, but are not limited to: template protein of interest production rate or culture titer, template protein of interest aggregation level, template protein of interest charge heterogeneity, template protein of interest size heterogeneity, glycosylation site occupancy and glycosylation profile for the template protein of interest, cell growth characteristics and cell metabolic characteristics, tertiary structure profile for the template protein of interest, template protein of interest self-association tendency, DNA sequence profiles, mRNA profiles, miRNA profiles, proteomic profiles and genomic stability of cells. This can in principle be performed in analogy with current CLD screening approaches used in the field. There initial screens of many clones using simple parallel culture formats and a few measured parameters such as titer and growth are followed by more extensive screening, including protein quality attributes as described above, of a lower amount of selected clones in more predictive culture formats such as shake flasks or bioreactors.

A second embodiment is based on directed evolution of the cells via pro-longed culture of the cells with recombinant expression pressure present. The high recombinant expression load imposed on all cells will have an impact on the viability and growth. Cells that do not handle the recombinant expression load well are hypothesized to be subjected to stress responses (amino acid shortage, charged tRNA shortage, hold up of the ribosomal machinery of recombinant mRNAs, hold up of the folding machinery on recombinant proteins, build-up of soluble or aggregated forms of recombinant protein within cells) reducing viability and growth. Further, cells having genetic/epigenetic changes leading to an improved handling of the recombinant expression load are hypothesized to have a higher viability and growth. Hence, by culturing cells for many generations, far exceeding what is used in typical CLD workflows, a large diversity of genetic/epigenetic changes are sampled and enrichment of cells having accumulated multiple positive changes are hypothesized based on this directed evolution mechanism.

Preferentially the TGOI codes for a template protein of interest representing an important class of proteins such as IgG1 antibodies or FC-fusion proteins and preferentially a difficult to express protein of this class to promote isolation of the highest possible production competency of the generated host cell line. Preferentially the culture of the cells is performed using conditions highly similar to a platform process defined for production of protein for clinical phases or commercial purposes to enable the adaptation through directed evolution to be directly compatible with these conditions. This could for example mean using a bioreactor fed-batch culture with defined culture medium, feed medium and process parameters. Pro-longed culture in this format could for example be achieved by inoculation of next generation cultures using a fraction of the culture from the previous culture. Prolonged culture could also be achieved in a chemostat reactor or a perfusion culture, potentially repeated multiple times using seeding of cells from a previous culture stage. Preferentially a selection marker, such as Neomycin resistance, a DHFR gene or a GS gene, is used together with culture conditions that put a strong selection pressure for the presence of an active selection marker. This could for example be the use of a neomycin resistance gene as selection marker and the use of neomycin during culture.

Another potential selection marker design could utilize a genetic circuit coupling cellular survival directly to expression of the TGOI. Such a genetic circuit could be based on non-native miRNAs binding both to a sequence stretch of TGOI mRNA and a sequence stretch on a selection marker gene such as NeoR, GS or DHFR. This is to further ensure, in addition to the use of a transcription hot spot region, that the expression construct is not silenced during culture leading to the enrichment of cells that are not expressing the template protein of interest. This approach has the potential to generate superior protein production clones as compared to approaches based on mere screening of clones. Typically in screening approaches a first culture is performed to select a first set of clones from. Individual clones are cultured for assessment followed by a second selection of clones. This is repeated a few times. As genetic variants are removed early and a low number of generations are allowed between selection steps a relatively low amount of genome variation is sampled using this approach. Using directed evolution and pro-longed culture for many generations keep all the genetic variation and allows time for accumulation of rare modifications and most importantly rare combinations of changes. Importantly, using this approach on a cell line lacking a TGOI would most certainly not lead to the same accumulation of positive protein production traits as most such changes would not be favored without the evolutionary pressure of high recombinant expression load and would not be possible to detect without the presence of a TGOI. Directed evolution and screening can also be combined and preferentially at least one final step including screening of production traits should be included. Intermediate screening steps in a workflow based on directed evolution can be used to further ensure that the rare event of clones having managed to silence the SM/TGOI does not lead to such cells being enriched in cultures. If the workflow starts with a clone screening and selection step a range of medium to high performance clones should preferably be selected for a round of culturing to ensure a large genetic diversity. Finally, a clone or a pool of cells isolated from any of these workflows is used to create a master cell bank (MCB) of a final improved host cell line. The final host cell line having accumulated genetic and/or epigenetic changes compared to the initial host cell line and recombinant mammalian host cell. In addition to the phenotypic diversity generated during cell growth, phenotypic diversity could also be artificially increased between selection/screening rounds by use of chemicals such as epigenetic de-regulators or by radiation increasing mutation rates.

Besides utilizing the natural or artificially enhanced plasticity in the genome to sample or promote random changes, a second approach based on targeted engineering can also be used to generate the final host cell line for CLD. A cell (C) according to FIG. 1a being subjected to a defined TGOI expression load is subjected to targeted changes to the genome (G) via the use of genome editing enzymes (such as Zinc finger nucleases, meganucleases, TALENs, CRISPR/Cas9 variants) and recombinant nucleic acid donor constructs to knock-out genetic functionality or add novel genetic functionality. After selection of cells having undergone correct/desired changes, the effect of these targeted changes is evaluated in follow up cultures to look at protein production traits such as those described above.

A range of different individual targeted changes can be evaluated and cells with targeted changes having positive effects on protein production traits can then be subjected to an iterative approach adding and evaluating additional changes. This process can be repeated until a final clone or cell pool with desired properties (based on the accumulation of one or multiple targeted changes) can be isolated. Preferentially the evaluation of protein production traits is performed using culture conditions highly similar to a platform process defined for production of proteins for clinical phases or commercial purposes to enable a fit to these conditions. This could for example mean using a bioreactor fed-batch culture with defined culture medium, feed medium and process parameters. Compared to targeted engineering approaches applied on host cell lines lacking a TGOI, the method according to the present invention enables several major advantages. First, the presence of a TGOI with controlled expression properties that can be reproduced for any GOI of the same class following CLD enables evaluation of targeted changes to be performed in conditions that are predictive of the intended final use. Secondly, the continuous presence of an expression load during the engineering workflow reduces the risk of loss of functionality due to genetic instability. As an added feature directed evolution, screening of natural genetic diversity and targeted changes can be combined in any form together with conditions predictable to the final use to generate the final improved host cell line. In one embodiment of the invention the instability of the host cell genome is first used to enable generation of an improved host cell via multiple genetic and/or epigenetic changes throughout the genome that would likely be difficult to generate using targeted engineering alone. In a second stage the instability of the genome is reduced either via directed evolution/selection or via targeted engineering. Research is currently underway to define engineering targets enabling stabilization of the genome of for example CHO cells [8].

As previously described the isolation/selection steps can also be repeated multiple times using a gradually increased expression load as outlined in FIG. 2. The rationale for a stepwise increase in the expression load is to enable a gradual move towards a higher performance phenotype. If the initial expression load is too high a low number of clones will be capable of matching this expression load and show up as competent producers during screening and hence a low number of clones can be passed on to a second round of growth and screening. This leads to an early potentially detrimental reduction of phenotypic diversity. There is a high risk for a low survival frequency and very low growth of cultured cells again leading to an inefficient sampling of clonal variation and slow accumulation of improved phenotypes. The initial clonal variation might not even be sufficient to enable survival of any cells at all. By gradually increasing the expression load cells can gradually adapt and an increased genetic variation can be sampled and taken forward in each iteration.

The use of a host cell line based on an improved cell generated using any of the above workflows together with expression vectors for Site-Directed Integration (SDI) enables a highly streamlined CLD workflow. Current methods known in the art are generally based on either random integration of expression constructs or targeted integration of expression constructs into a genomic location having a SM region only. Using the random integration approach a pool of cells that are all actively transcribing genes in the expression construct can be generated via the aid of a selection marker. However, different clones will have the expression construct integrated at different genomic locations and with different number of copies. This in turn will result in a range of transcription levels and importantly different clones will also display varying stability of transcription over time and during different culture conditions. In addition different clones will display different protein production traits. In summary this leads to a need of massive screening efforts to isolate a clone with both good transcription levels and good protein production traits.

Furthermore, repeating the CLD using either an identical expression construct or a variant expression construct will lead to cells that are different at the genetic and phenotypic level making it difficult to evaluate optimal expression construct and GOI designs. Using a targeted approach simplifies the workflow by the introduction of a single copy of the expression construct into a pre-defined/pre-characterized genomic location. The delivery of the expression construct to the defined location is aided by the presence of specific sequences at the genomic location and in the expression constructs and via the co-transfection of a vector coding for a nucleic acid enzyme. The enzyme can either be a nuclease introducing a double strand break unique to the genomic location and integration proceeds via homologous recombination between a long stretch of homologous sequences present at the genomic site and in the expression construct. As an alternative, shorter specific nucleotide sequences acting as target sequences for recombinases can be present at the genomic location and in the expression construct. The co-transfected recombinase will then catalyze the integration of the expression construct. After utilizing selection via a second SM set a pool of cells all carrying a single copy of the expression construct and displaying similar transcription levels can be generated. However, different clones will still display different protein production traits and hence there is a need for a clone screening procedure to isolate a cell with the desired traits. Although the screening should be reduced as compared to random integration it could still be a significant effort and cells can still be different between different CLD efforts.

However, using the host cell line and the CLD methodology of the present invention potentially removes both of the above sources for variation and screening need and can potentially generate production clones/pools with superior production traits as compared to current screening based methods. An improved host cell generated according to any combination of the approaches described above already displays the desired protein production traits and has a Landing Pad region containing sequences enabling targeted insertion of a desired gene of interest at the desired genomic location previously used to express the TGOI. This can be performed in different ways as described in general terms above and in detail later but all workflows generally use some sort of selection marker. After selecting for proper insertion of the GOI a pool of cells with limited diversity is generated. In principle, a clone from this pool could be isolated without further screening and only characterized to ensure that a single correct GOI construct has been inserted and no additional random integration.

Some examples of improvements over standard workflows have been described in previous art. First, directed evolution of a final host cell line has been proposed [9]. However, in this case directed evolution is performed on an initial cell line lacking the introduction of recombinant genes or a hot spot integration site and selection traits are not directly linked to protein production traits. Further, the generated host cell line is then utilizing random integration for CLD. Host cells generated using this approach will not have been subjected to a pressure to accumulate changes improving protein production traits and as adaptation to specific culture conditions has been done without the recombinant expression burden there is a risk for sub-optimal adaptation to the conditions experienced during production of a recombinant protein.

The present invention represents several improvements over this approach. The presence of the TGOI enables selection/evolution of protein production traits matching the combined demands of the specific culture conditions and a high level recombinant expression pressure. Further, the continuous presence of the TGOI reduces the risk for loss of adaptation due to genetic instability. Finally, the cassette exchange approach to CLD enables the conditions experienced by the cells following introduction of the GOI (at the same location, with the same copy number and with the same sequence elements) to be highly similar to the conditions used during generation of the host cell line. Utilization of pre-adapted cells has also been proposed for targeted integration based CLD [10]. In this approach it is proposed that a cell line generated using random integration CLD and displaying desired protein production traits should be selected as a source for generating a final host cell line. In the proposed procedure, the genomic location is identified (must be a single site) and the recombinant constructs are cut out using gene editing based homologous recombination and exchanged for a construct carrying a selection marker flanked by recombinase sequences.

After isolation of cells having undergone correct exchange, the genomic site is treated with a recombinase to cut out the selection marker and leave a single recombinase site flanked by a promoter. This host cell line can then be used for targeted integration of a second expression construct. In this approach there is not a match between the expression load provided by the multiple copies of the first expression construct and the single copy of a second expression construct following CLD. Hence, the properties of the host cell line are not likely to be fully suitable to the new conditions. This mismatch can be further increased if the culture conditions are different between the initial cell line and the second cell line. In addition, after the exchange of the original expression construct there are multiple culture periods during both the construction of the host cell line and each CLD effort where the lack of recombinant expression load can lead to loss of accumulated traits and increased diversity of cells due to genetic instability. Hence, the current invention offers multiple improvements over this approach in that the selection/evolution of traits can be better matched between host cell line and the cell line producing the GOI after CLD. In addition the presence of the TGOI or the GOI at a similar expression load throughout all culture steps minimize the risk of loss of functionality/increased cell diversity due to genetic instability. In addition the increased sampling of diversity possible by directed evolution and the possibility to add targeted modifications has the potential to generate production clones with superior protein production traits.

Using the natural diversity of cells has recently been discussed and highlighted as a potentially superior approach in a GEN article [13]. Using selection to generate a high performance cell expressing a certain template protein is here contemplated. However instead of isolating this cell and using it directly in subsequent CLD workflows the potential to identify engineering targets by detailed omics characterization to enable reproduction of a high productivity cellular phenotype using targeting engineering approaches is proposed.

Figure 3:
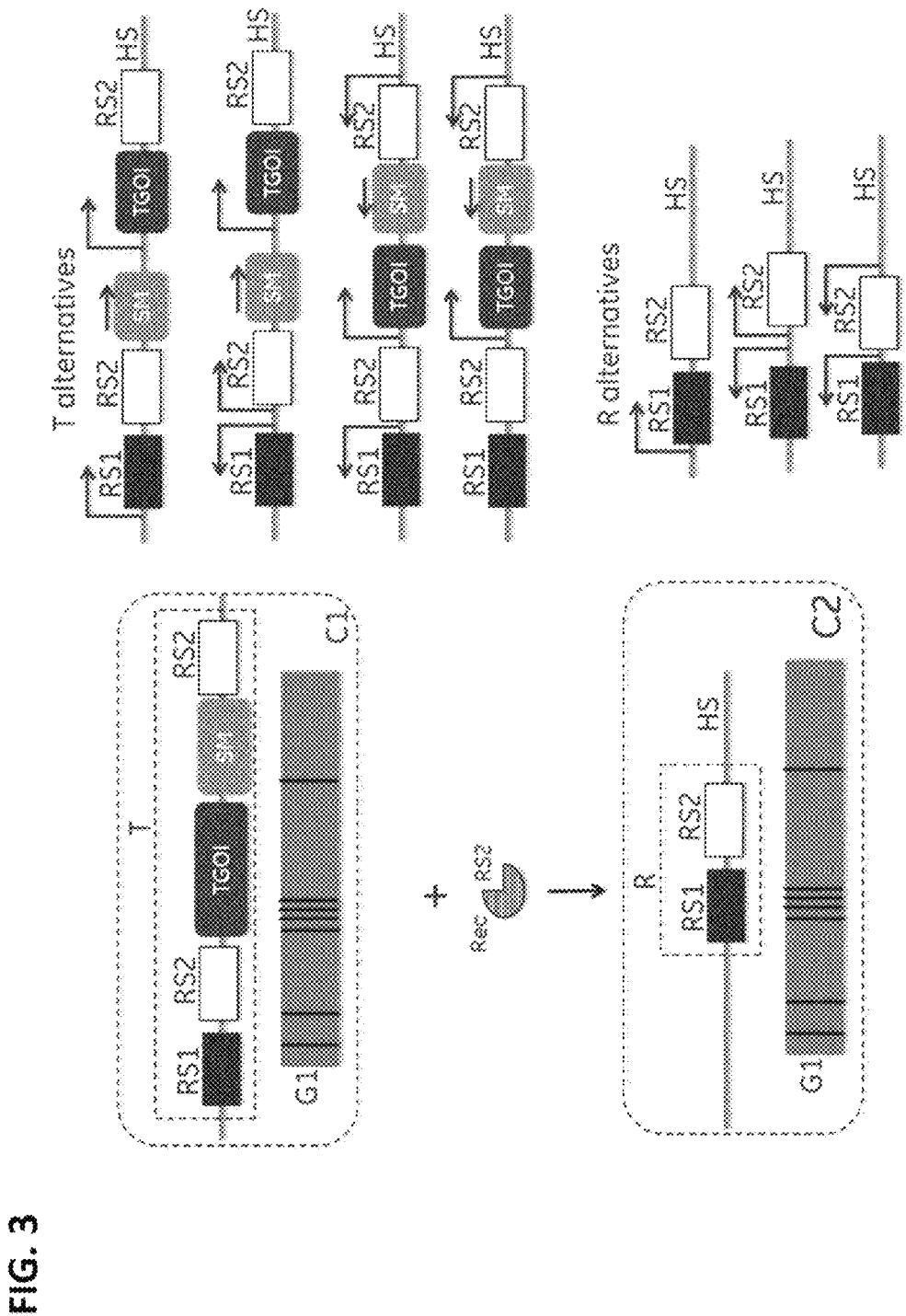
FIG. 3 describes generation of the improved cell C2 carrying a receiving DNA construct R using a recombinase (Rec-RS2) to excise a TGOI region being flanked by reversible recombinase target sequences RS2.
Figure 5:
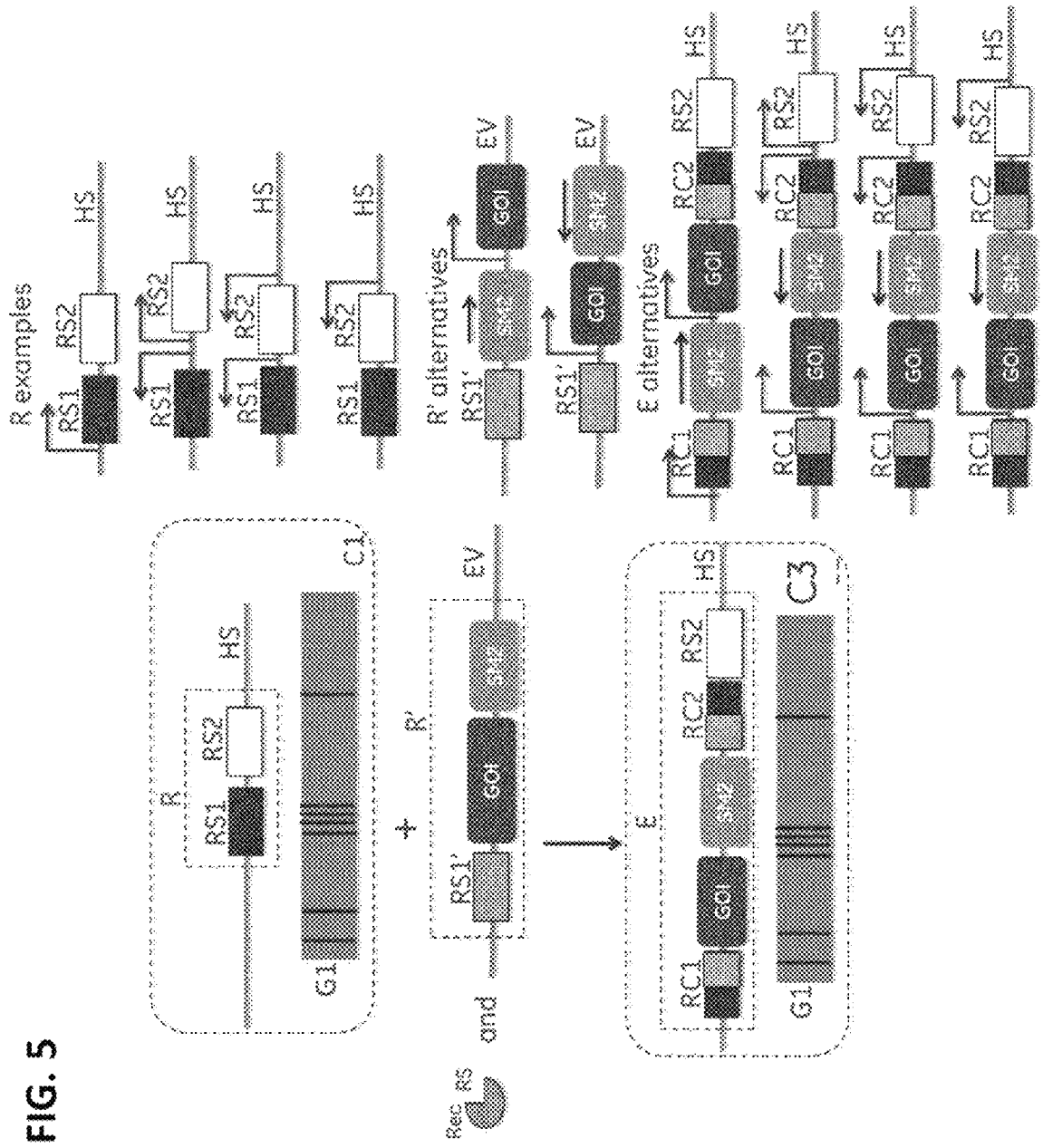
FIG. 5 describes cell line development using the cell C2 as generated in FIG. 3 and highlighting alternative designs possible dependent on promoter and SM placement.

Following the detailed outline of the general concept of the invention and its benefits above specific implementations will now be described. In a first specific implementation the improved cell C2 (Cn+1) carrying a receiving DNA construct R is generated according to FIG. 3 or FIG. 4 using a recombinase (Rec-RS2) to excise a TGOI region being flanked by reversible recombinase target sequences RS2. CLD using these improved cells are outlined in FIG. 5. The cell C2 containing one irreversible recombinase recognition sequence (RS1) and one reversible recombinase recognition sequence (RS2) is contacted with a recombinase with specificity for RS1/RS1' and a matching Expression Vector (EV) containing a recombinant DNA construct R' with a matching irreversible recombinase recognition sequence RS1' a desired gene of interest (GOI) and a selection marker (SM2). Following insertion a cell or a pool of cells having undergone correct modification is selected using the selection marker (SM2). The recombinases used can be of any reversible and irreversible type such as attP/attB/PhiC31 as an irreversible system and loxP/Cre as an reversible system.

Figure 7:
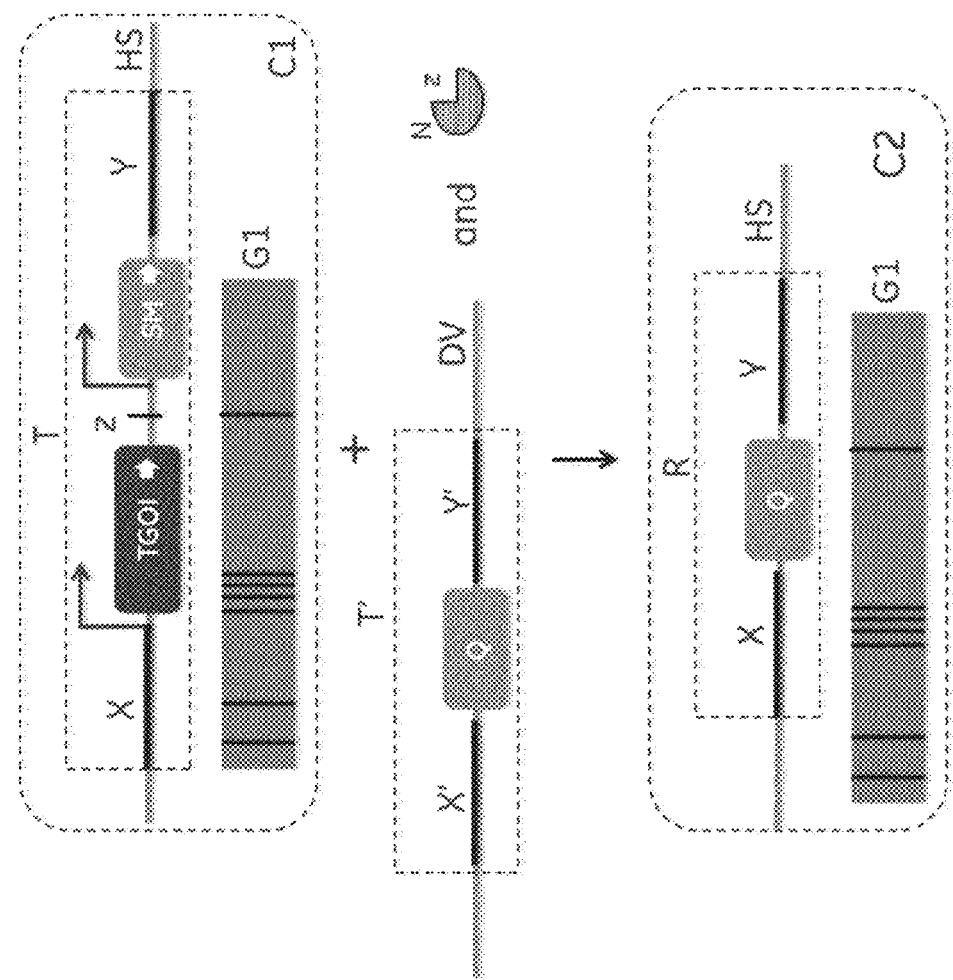
FIG. 7 describes modifying the template recombinant DNA construct T of the improved cell C1 to a cell C2 carrying a receiving recombinant DNA construct R being ready for Cell Line Development via the use of Double Strand Break Induced Homologous Recombination (Gene Editing)

In a second set of specific implementations, the template recombinant DNA construct T of the improved cell C1 is modified to a receiving recombinant DNA construct R (generating the cell C2) via the use of gene editing approaches as outlined in FIG. 7. The improved cell C1 contains two long sequences (>300 bp and typically >=1 Kb) X and Y flanking the template gene of interest and an optional selection marker and being unique or rare in the genome G1. Further the flanked region contains an additional shorter sequence z (15-40 nt) being unique or rare in the genome G1. As C1 is contacted with a donor vector (DV) containing a recombinant DNA construct T' and a site specific gene editing DNA nuclease with specificity for z (Nz) a cassette exchange between T and T' occurs via homologous repair mechanisms catalyzed by a double strand break at z. The two sequences X' and Y' are identical or highly homologous to the sequences X and Y in the genome G1. The resulting recombinant DNA construct R contains sequences Q enabling targeted integration of a GOI into the hot spot region HS. The site specific nuclease can be based on any gene editing solution such as zinc finger nucleases, homing endonucleases, TALENs or CRISPR/Cas9 variants or other CRISPR systems.

Figure 8:
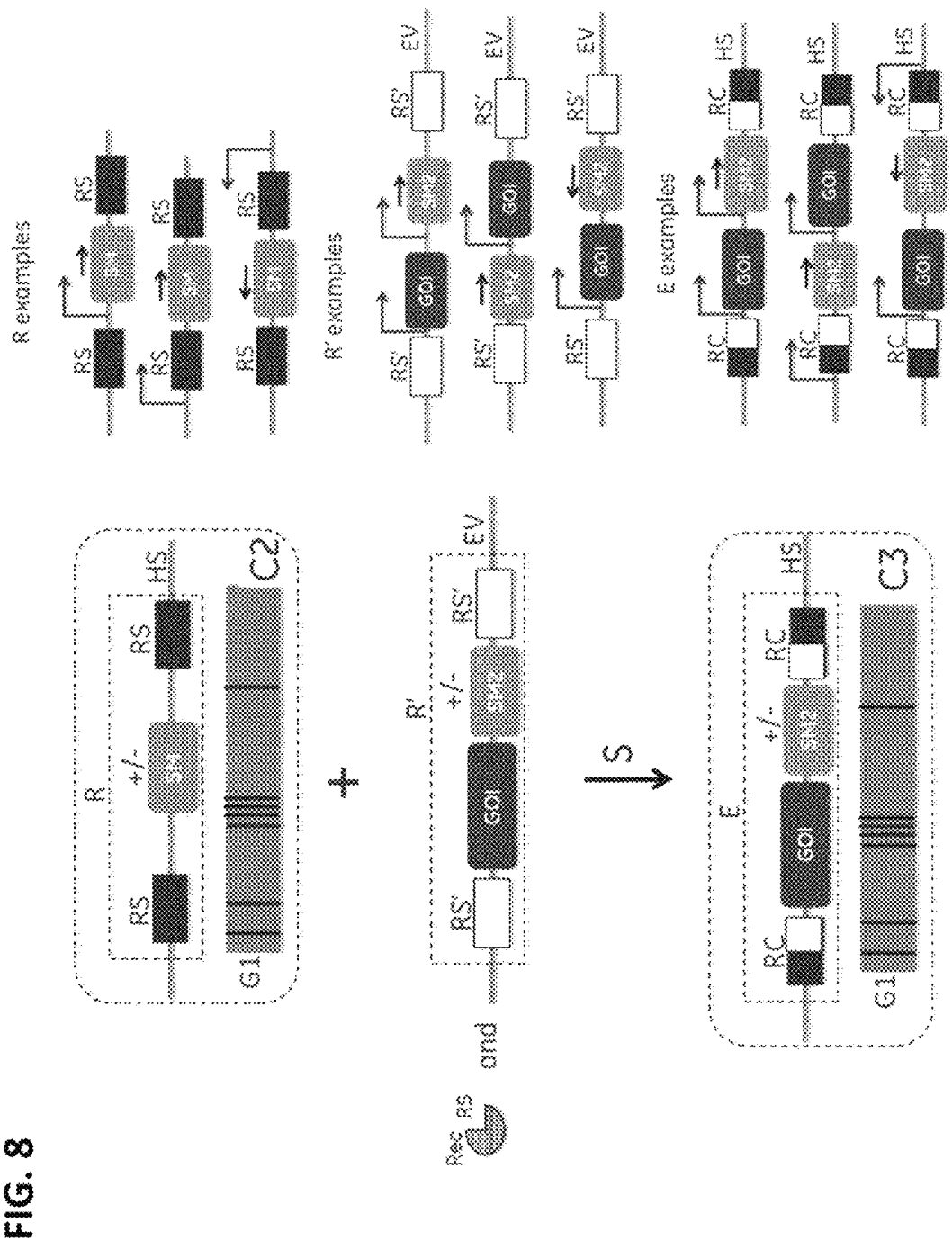
FIG. 8 describes cell line development using different promoter placements in an improved cell C2 carrying a cassette exchange design based on two recombinase recognition sequences (RS)

One approach utilizes a receiving DNA construct design R in which an optional SM gene(s) are flanked by two recombinase recognition sequences (RS) and an expression vector design in which a GOI(s) and an optional second SM gene(s) are flanked by matching recombinase recognition sequences (RS'). By co-transfecting the improved cell C1 with the expression vector in the form of a plasmid and a plasmid encoding a recombinase (Rec-RS) with specificity for RS/RS+ a cassette exchange between R and R' is achieved. A cell C3 having undergone the correct exchange only can be selected via the difference in SMs between R and R'. The resulting recombinant DNA construct E contains recombined recombinase recognition sequences RC. Depending on the recombinase system used these can either be different from RS and RS' and differ between the 5' and 3' sequences (as for attP/attB/PhiC31) or be identical to RS/RS' (as for loxP/Cre). The recombinase recognition sequences used can be of any type such as a serine recombinase type such as attP/attB or a tyrosine recombinase type such as Lox, Rox or FRT together with matching recombinases such as PhiC31, Cre, Dre, or Flp. Different examples of this approach based on varying the promoter placement for R and R' are outlined in FIG. 8.

Figure 9:
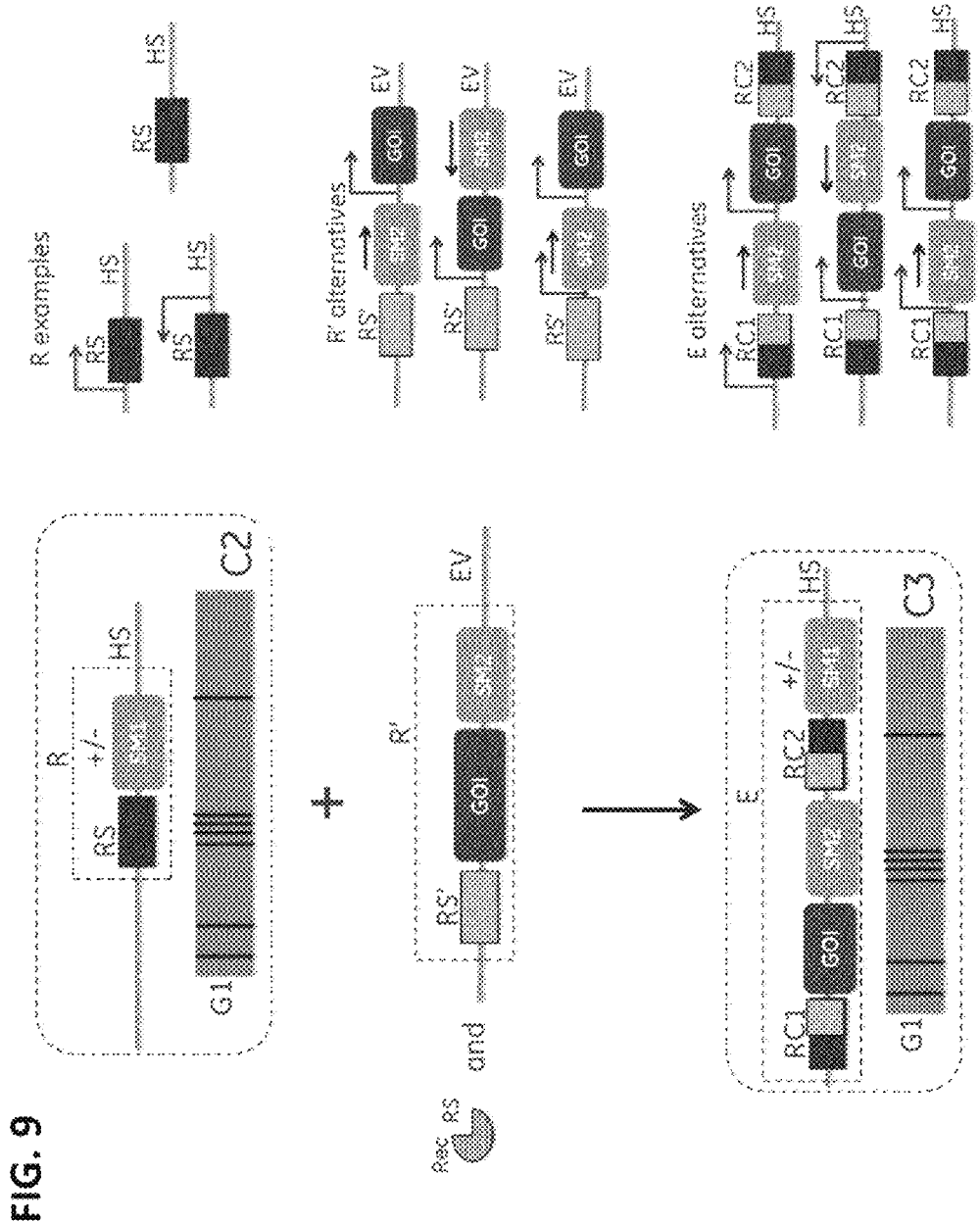
FIG. 9 describes cell line development using different promoter placements in an improved cell C2 carrying a single recombinase recognition sequences (RS).

In another approach the receiving DNA construct R contains a single recombinase recognition sequence RS followed by an optional SM gene(s) and the matching expression vector EV a single matching recombinase recognition sequence RS' followed by a GOI(s) and a SM gene(s) in any order. By co-transfecting the improved cell C1 with the expression vector in the form of a plasmid and a plasmid encoding a recombinase (Rec-RS) with specificity for RS/RS' the R' construct is introduced into the cell and simultaneously changing the relative position of the original R construct so that the resulting E recombinant DNA construct is a combination of R and R'. Different examples of this approach based on varying the promoter placement for R and R' are outlined in FIG. 9.

In any of the above embodiments of the invention the TGOI/GOI could contain a single gene of interest coding for proteins such as growth factors, blood clotting factors, cytokines, hormones, erythropoietins, albumins, virus proteins, virus protein mimics, bacterial proteins, bacterial protein mimics, domain antibodies, ScFvs, Affibodies, DARPINs, multimerization domains, IgG Fc domains, albumin binding domains, Fc receptor binding domains or fusion proteins based on combinations of the above single gene of interest coded protein classes. The TGOI/GOI could also contain two or more genes of interest coding for proteins such as monoclonal antibodies based on naturally occurring scaffolds, bi-specific antibodies based on naturally occurring scaffolds, Fabs, virus like particles, multiple chain proteins based on association of two or more different protein chains selected from the list of single gene coded proteins above. In preferred embodiments of the invention the TGOI of the host cell line and the GOI used for CLD encode proteins belonging to the same protein class. In further preferred embodiments the TGOI is a hard to express protein of that protein class.

In further preferred embodiments a single copy of TGOI and GOI is used. In further preferred embodiments genetic elements, such as promoter(s), 5'-UTR(s), signal peptide(s), design principle for synonymous nucleotide encoding in the coding region and 3'-UTR(s), used in the TGOI and GOI are identical. In some embodiments multiple final host cell lines containing different TGOIs of the same protein class but with different amino acid ratios are available and the specific cell line used for CLD using a specific GOI is selected based on closest match between amino acid ratios of the template protein of interest (encoded by TGOI) and the desired protein of interest (encoded by GOI). In some embodiments multiple final host cell lines containing identical TGOIs but selected/derived to display a specific protein quality profile, such as a specific glycoprofile, are available. The specific cell line used for CLD using a specific GOI is selected based on closest match between desired protein quality profile and available protein quality profiles.

REFERENCES

[1] Hacker, D. L., De Jesus, M., Wurm, F. M., 2009. 25 years of recombinant proteins from reactor-grown cells—where do we go from here? Biotechnology Advances 27, 1023-1027.
[2] Wirth, D., et al., Road to precision: recombinase-based targeting technology for genome engineering. Current Opinion in Biotechnology, 2007.
[3] D. Wirth, L. Gama-Norton, R. Schucht, K. Nehlsen "Site-Directed Engineering of Defined Chromosomal Sites for Recombinant Protein and Virus Expression—Site-directed engineering of defined chromosomal sites", BioPharm International, Volume 22, Issue 7 (2009)
[4] Alexandra Baer and Jürgen Bode, Coping with kinetic and thermodynamic barriers: RMCE, an efficient strategy for the targeted integration of transgenes, Current Opinion in Biotechnology 2001, 12:473-480
[5] Wei-shou Hu; Cell Culture Bioprocessing Engineering; ISBN 978-0-9856626-0-8, pages 127-146
[6] WO2009/075886 (Translation Enhancer Elements, TEEs)
[7] WO2010/98861 (RESCUE)
[8] www.chorus.co.at/projects/genomic-stability-of-the-host-cell-line.html, Dec. 3, 2014
[9] Nazanin Dadehbeigi et al.; Robust and efficient recombinant mAb production using a proprietary CHO host cell with improved characteristics identified through directed evolution, conference poster www.fujifilmdiosynth.com/pdfs/CCE_XIV_Poster_Fay_Saunders.pdf
[10] Eric Rhodes; Gene editing approaches for viable commercial production; conference presentation Bioprocess summit Boston August 2012
[11] U.S. Pat. No. 6,632,672 (Stanford att-site patent).
[12] A Brown et al.; Synthetic promoters for CHO cell engineering; Biotechnology and Bioengineering vol 111 (8) 1638-1647 (2014).
[13] Angelo DePalma; Cell-Line Optimization: Nature or Nurture? Are Great Cell Lines Born or Made? Both!; GEN Nov. 1, 2015 (Vol. 35, No. 19)

The invention claimed is:

1. A method to obtain a cell suitable for expressing a protein of interest comprising the following steps:
a) integration of a nucleic acid molecule comprising a polynucleotide encoding a first protein of interest into a pre-defined site in the genome of a recipient cell, wherein the nucleic acid molecule comprises in 5' to 3' sequence order:
a first recombinase recognition sequence;
a first copy of a second recombinase recognition sequence;
a promoter-less selection marker gene and the polynucleotide encoding the first protein of interest, wherein the promoter-less selection marker and the polynucleotide encoding the first protein of interest are in any order and orientation; and
an additional copy of said second recombinase recognition sequence, wherein the first and the second recombinase recognition sequences are recognition sequences for different recombinases;
b) identification of cells expressing the first protein of interest;
c) excision of the nucleic acid molecule comprising a polynucleotide encoding the first protein of interest from the genome of the identified cells to provide a resulting cell containing the first recombinase recognition sequence and a copy of the second recombinase recognition sequence enabling targeted introduction of a nucleic acid molecule encoding a second protein of interest into said pre-defined site in the genome; and
d) subsequent to step c), integration of the nucleic acid molecule encoding the second protein of interest into the pre-defined site in the genome of the resulting cell.

2. The method according to claim 1, further comprising creation of a cell line suitable for production of said second protein of interest as a recombinant protein.

3. The method according to claim 2, wherein the recombinant protein is an active pharmacological ingredient.

4. The method according to claim 2, further comprising providing the recombinant protein as an ingredient in a diagnostic reagent.

5. The method according to claim 2, further comprising providing the recombinant protein as a reagent in an industrial process.

6. The method according to claim 1, wherein the first protein of interest is a fluorescent protein.

7. The method according to claim 1, wherein the first protein of interest is an immunoglobulin or immunoglobulin-like protein.

8. The method according to claim 1, further comprising selecting a cell with increased capacity to express the first protein of interest relative to other cells identified as expressing the first protein of interest prior to excision of the nucleic acid molecule comprising a polynucleotide encoding the first protein of interest.

9. The method according to claim 8, wherein selecting the cell with increased capacity to express the first protein of interest comprises isolating clones from a culture of said identified cells expressing the first protein of interest.

10. The method according to claim 8, wherein selecting the cell with increased capacity to express the first protein of interest comprises isolating pools or clones from said identified cells expressing the first protein of interest after (1) different culture time in a continuous culture format such as a perfusion culture or (2) different number of individual cultures starting with inoculation of a first culture using said identified cells expressing the first protein of interest and using a volume from a finished culture to inoculate a next culture or (3) a combination of (1) and (2).

11. The method according to claim 8, wherein selecting the cell with increased capacity to express the first protein of interest comprises performing targeted engineering by applying gene editing methods to introduce, remove or modify genetic material in the genome of said identified cells expressing the first protein of interest.

* * * * *